United States Patent
Mordaunt et al.

(10) Patent No.: US 7,873,083 B2
(45) Date of Patent: Jan. 18, 2011

(54) SYSTEM, METHOD, AND APPARATUS TO PROVIDE LASER BEAMS OF TWO OR MORE WAVELENGTHS

(75) Inventors: David Haydn Mordaunt, Los Gatos, CA (US); Steven Scott Christensen, Fremont, CA (US); Allison Albrecht Ferro, Fremont, CA (US); David A. Dewey, Sunnyvale, CA (US)

(73) Assignee: Lumenis Ltd., Yokneam (IL)

( * ) Notice: Subject to any disclaimer, the term of this patent is extended or adjusted under 35 U.S.C. 154(b) by 823 days.

(21) Appl. No.: 10/531,691

(22) PCT Filed: Oct. 16, 2003

(86) PCT No.: PCT/US03/29132

§ 371 (c)(1),
(2), (4) Date: Apr. 23, 2007

(87) PCT Pub. No.: WO2004/036705

PCT Pub. Date: Apr. 29, 2004

(65) Prior Publication Data

US 2007/0230520 A1 Oct. 4, 2007

Related U.S. Application Data

(60) Provisional application No. 60/418,719, filed on Oct. 17, 2002.

(51) Int. Cl.
*H01S 3/10* (2006.01)
(52) U.S. Cl. .................. 372/23; 372/29.011; 372/97
(58) Field of Classification Search ............ 372/23, 372/29.011
See application file for complete search history.

(56) References Cited

U.S. PATENT DOCUMENTS 5,144,630 A * 9/1992 Lin .............................. 372/22

(Continued)

FOREIGN PATENT DOCUMENTS

EP 1 139 521 10/2001

(Continued)

OTHER PUBLICATIONS

Supplementary European Search Report for EP 03 75 9272 mailed Feb. 24, 2006.

(Continued)

*Primary Examiner*—Dung T Nguyen
(74) *Attorney, Agent, or Firm*—Mintz Levin Cohn Ferris Glovsky and Popeo, P.C.

(57) ABSTRACT

A system, apparatus, and method may provide laser beams of two or more wavelengths from diode pumped solid-state laser sources (220, 222, 224). The beam paths of these laser beams with different wavelengths, which are generated by the laser sources (220, 222, 224), may be aligned along a common optical axis 280 by an optical configuration, to treat at least one target area. Frequency-doubled laser beams, output from a plurality of diode pumped solid state laser cavities, may be passed through fold mirrors (M2, M5, M8), and combined on a common optical axis 280, using one or more combiner mirrors (M10, M11, M12), to unify the beam paths. Selected laser beams may be delivered to a target using one or more delivery systems.

29 Claims, 6 Drawing Sheets

U.S. PATENT DOCUMENTS

| | | | | |
|---|---|---|---|---|
| 5,291,505 | A | * | 3/1994 | Nielsen ................... 372/38.03 |
| 5,317,348 | A | | 5/1994 | Knize et al. |
| 5,830,514 | A | * | 11/1998 | Barenboim et al. ...... 425/174.4 |
| 6,008,781 | A | * | 12/1999 | Furness et al. .................. 345/8 |
| 6,066,127 | A | | 5/2000 | Abe et al. |
| 2001/0055462 | A1 | * | 12/2001 | Seibel ......................... 385/147 |
| 2003/0179344 | A1 | * | 9/2003 | Van de Velde .............. 351/200 |

FOREIGN PATENT DOCUMENTS

| | | |
|---|---|---|
| GB | 1 343 931 | 1/1974 |
| WO | WO 98/35504 * | 8/1998 |
| WO | WO 02/27872 | 4/2002 |

OTHER PUBLICATIONS

PCT International Preliminary Examination Report from PCT/US03/29132, dated Mar. 16, 2005.

International Search Report from PCT/US03/29132, dated Feb. 23, 2004.

Supplementary European Search Report from EP 03759272, dated Feb. 13, 2006.

\* cited by examiner

SYSTEM, METHOD, AND APPARATUS TO PROVIDE LASER BEAMS OF TWO OR MORE WAVELENGTHS

CROSS-REFERENCE TO RELATED APPLICATIONS

This application is a National Phase Application of PCT International Application No. PCT/US2003/029132, International Filing Date Oct. 16, 2003, claiming priority of U.S. Provisional Patent Application, 60/418,719, filed Oct. 17, 2002.

FIELD OF THE INVENTION

Embodiments of the present invention relate generally to laser devices and methods, and more particularly to systems, methods and apparatuses that provide two or more laser beams of different wavelengths.

BACKGROUND OF THE INVENTION

Intense light energy, such as a laser beam, can be used for photocoagulation and endo-photocoagulation, for example, to perform surgical coagulation of tissue to destroy abnormal tissues or to form adhesive scars, especially in ophthalmology. Diode-pump solid state (DPSS) lasers, which are known and are used in many applications, for example, in treatment by illumination of body tissue, are increasingly being used for precision, fine machining procedures and treatments.

Pumped-light laser sources, e.g., diode lasers, are generally more efficient than conventional laser sources. DPSS lasers are particularly useful because they can be designed to emit at essentially any wavelength within a wavelength range determined by the specific semiconductor materials used for their manufacture.

SUMMARY OF THE INVENTION

There is provided, in accordance with an embodiment of the present invention, an apparatus, system, and method to provide laser beams of two or more wavelengths from two or more diode pumped solid state (DPSS) laser sources. According to some embodiments of the present invention, a laser illumination system that includes a laser sub-system may be provided. For example, the laser sub-system may include a module with two or more DPSS laser cavities to produce beams of two or more respective wavelengths, and an optical configuration to align the paths of these two or more laser beams along a common optical axis using, for example, fold mirrors and combiner mirrors.

In accordance with an embodiment of the present invention, an optics sub-system may be used to control and channel selected laser beams, for example, laser beams of two or more respective wavelengths, to one or more delivery systems. One or more delivery systems may deliver the laser beams to one or more selected targets.

Furthermore, in accordance with an embodiment of the present invention, a method is provided to produce laser beams of two or more wavelengths from two or more DPSS laser sources, align the paths of the laser beams along a common optical axis, and select at least one laser beam with a desired wavelength to deliver to at least one target area. Such a method may include combining the paths of frequency-doubled light beams from two or more diode pumped solid state laser cavities on a substantially common optical axis.

In accordance with an embodiment of the present invention, a method is provided to operate the laser illumination system, at one or more wavelengths selected from two or more wavelengths generated by two or more respective DPSS laser cavities.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1A:
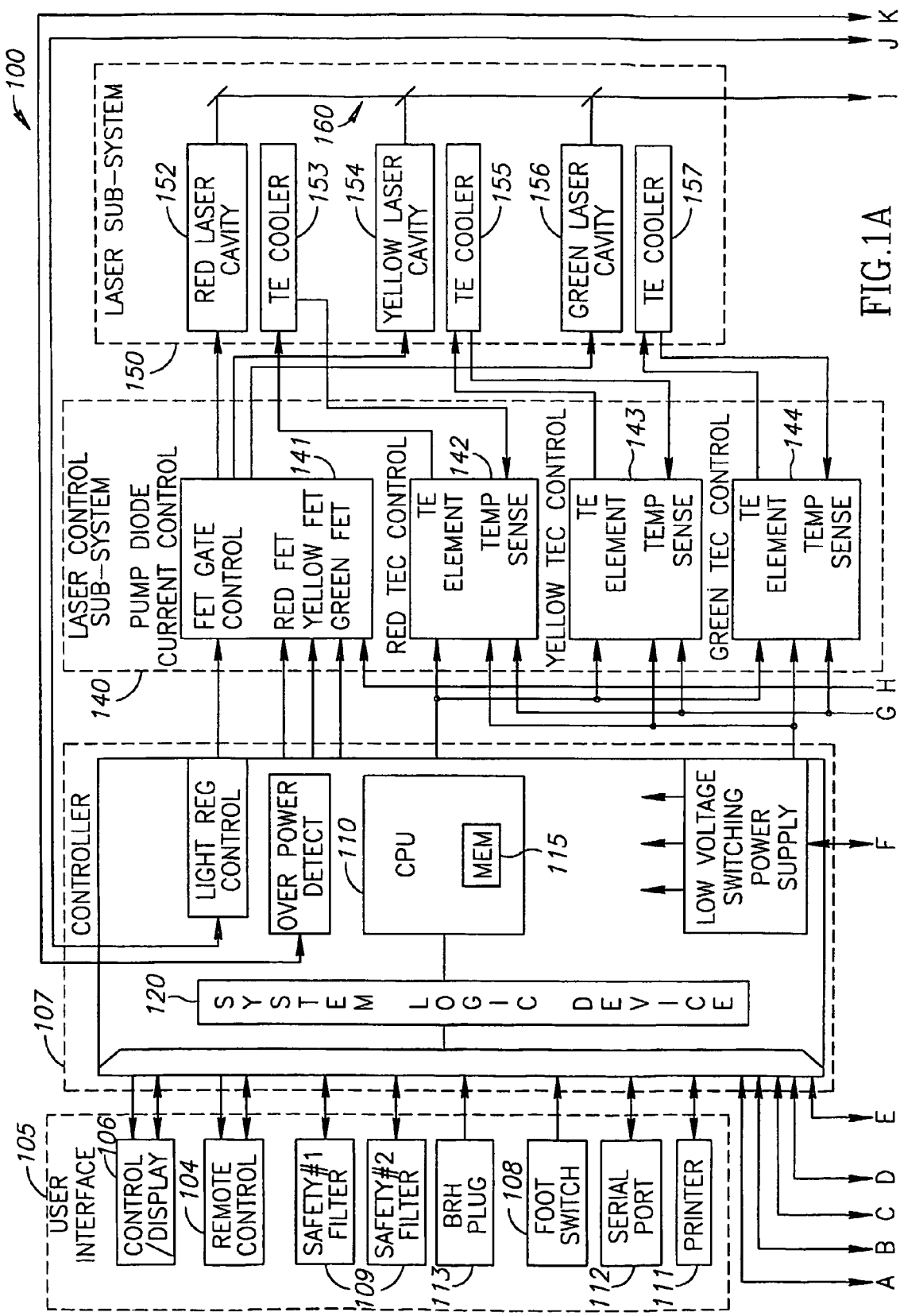
FIGS. 1A and 1B are a schematic block diagram illustration of an exemplary illumination system, according to at least one aspect of an embodiment of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Embodiments of the present invention may enable an apparatus, system, and method for selectively providing beams of two or more wavelengths generated by two or more independent DPSS laser sources.

Figure 1B:
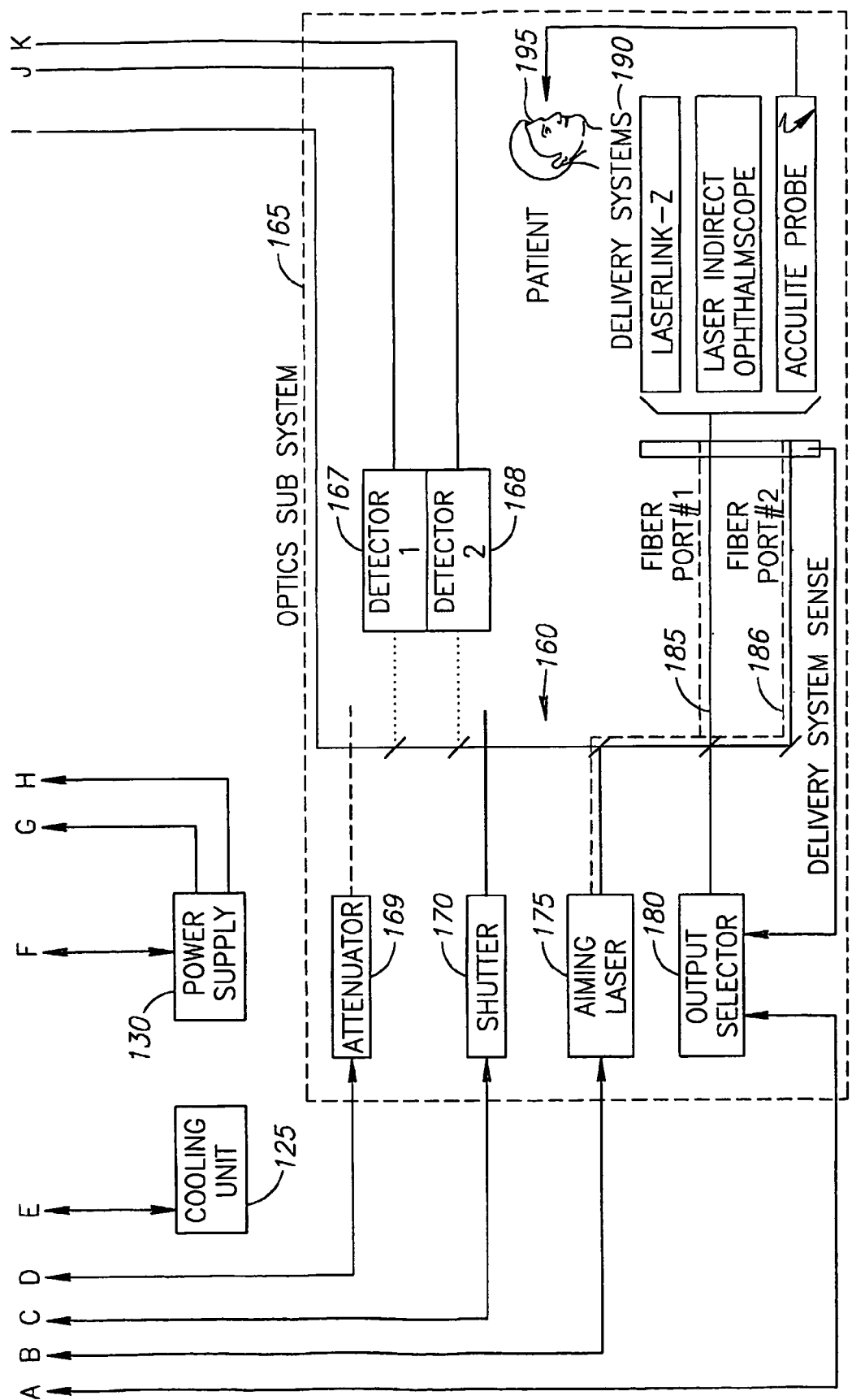

Reference is now made to FIGS. 1A and 1B, which schematically illustrate an exemplary laser illumination system 100, according to at least one aspect of an embodiment of the present invention. As can be seen in FIG. 1A, laser illumination system 100 may include a user interface 105 to enable a user to operate system 100, a controller 107 to control operation of system 100, and a laser control sub-system 140 to control the laser energy provided by a laser sub-system 150.

Laser sub-system 150 may enable generation of laser beams of two or more wavelengths by two or more respective laser cavities, and align the paths of the outputted laser beams with differing wavelengths along a common optical axis. As can be seen in FIG. 1B, system 100 may further include an optics sub-system 165, to control, channel and deliver selected laser beams to one or more selected targets.

User interface 105 may include, for example, a control and display panel 106, which may include, for example, a LCD display device, a touch screen interface, and any other suitable associated input devices, to enable a user to operate system 100. User interface 105 may further include a remote control unit 104, a footswitch 108, and additional interactive controls, such as input and output devices, to enable a user, such as a medical practitioner, to interface with system 100. Additional components of user interface 105 may include one or more eye safety filters 109, BRH plug 113, printer 111, at least one serial port 112, and/or operating software. Other activation means, components, units, and/or accessories etc. may be used.

Controller 107 may include a processor or CPU 110 with control electronics, to enable data processing and control of system 100. CPU 110 may include hardware, an embedded micro controller, and/or software, etc., to control and monitor functions within laser illumination system 100, and to control user initiated instructions. In addition, hardware and/or software for monitoring laser safety critical functions, as are known in the art, may be integrated into CPU 110. CPU 110 may include a memory unit 115, which may store, for example, system data and executable code for operating system 100. Controller 107 may include a system logic device, such as, for example, an electrically programmable logic device (EPLD) 120, or any other suitable component, to enable programming and execution of system logic according to usage requirements. CPU 110 may be adapted to process results of actual laser beam output, for example, from a main photocell or detector 167 and/or a safety photocell 168 in optics sub-system 165, as described in detail below. CPU 110 may utilize such processed data to instruct laser control sub-system 140 to adjust the outputs of laser cavities 152, 154 and/or 156 to achieve a desired laser beam output.

System 100 may include a power supply 130 to supply the electric power to the system 100 or part thereof. For example, power supply 130 may control voltage supplied to CPU 110 or to components of laser control sub-system 140 etc. A cooling unit 125 may be provided to cool controller 107 or part thereof, as well as to cool components of a pump diode current control unit 141.

Laser control sub-system 140, the operation of which may be controlled by CPU 110, may control laser energy generation by, for example, laser cavities 152, 154, and 156. Laser control sub-system 140 may include pump diode current control unit 141 to control the provision of electric current to laser cavities 152, 154, and 156, respectively, using a field effect transistor (FET) gate. Laser control sub-system 140 may include at least one TEC control unit, such as, for example, a red TEC control unit 142, a yellow TEC control unit 143, and a green TEC control unit 144, to provide precise temperature control for enabling stable laser output from laser cavities 152, 154, and 156, respectively. Such TEC control units may control respective thermo-electric (TE) cooler units, for example, TE cooler units 153, 155 and 157 located in laser capsules 152, 154 and 156, respectively. TEC control units 142, 143 and 144 may receive feedback, for example, temperature sensing data, from TE cooler units 153, 155 and 157 respectively.

Laser sub-system 150 may include two or more laser cavities, for example, cavities 152, 154 and 156, to generate light beams of different wavelengths. Cavities 152, 154 and 156 may include, for example, red, yellow, and green diode pumped solid-state laser sources and respective frequency doubling sections, as are described in detail below. Cavities 152, 154 and 156 may be associated with TE coolers, for example, coolers 153, 155 and 157, respectively. Laser sub-system 150 may further include an optical configuration 160 to align the paths of the outputted laser beams along a common optical axis, as is described in detail below.

Optics sub-system 165, which may be used to control, channel and deliver selected laser beams to one or more selected targets, may include an attenuator 169 to attenuate outgoing pulses, and/or a shutter 170 to control or limit outgoing laser pulses. Optics sub-system 165 may further include at least one power-monitoring device, such as, for example, main photocell 167 and safety photocell 168, which are capable of sampling the output energy of outputted laser beams. Sampled data, for example, may be transferred from main photocell 167 and/or safety photocell 168 to controller 107, where the data may be processed. Optics sub-system 165 may further include an aiming laser 175, such as, for example, a diode aiming beam laser, to enable a user of system 100 to aim laser pulses at one or more targets, as is known in the art. Optics sub-system 165 may include an output selector 180 to select desired laser beam outputs. One or more optical ports, such as optical ports 185 and 186, may be provided to channel outputted laser beams to one or more delivery systems 190. Delivery systems 190, which may include optical fibers, may enable delivery of two or more beams of different wavelengths to different targets, for example, in an ophthalmic tissue of a patient 195.

An exemplary embodiment of an aspect of the present invention may include two or more laser diodes, for example, three diode pumped solid state (DPSS) laser sources, within laser cavities 152, 154 and 156, which may provide, for example, green, yellow, and red laser beams. In some exemplary embodiments the laser beam wavelengths that may be output by system 100 may include wavelengths of about 532 nm, about 561 nm, and about 659 nm. Other structures and dimensions may be used, for example, to provide different wavelength values, a different number of different wavelengths and/or desired combinations of one or more wavelengths Delivery systems 190 may include, for example, standard commercially available Zeiss style examination slit lamp(s), endoprobes, and indirect ophthalmoscopes etc. Delivery systems 190, which may be constructed from fiber optics or other optical media, may be attached to user interface 105 at either or both of optical ports 185 and 186 etc. Examples of delivery devices that may be used in conjunction with embodiments of the present invention may include Laserlink-Z, manufactured by Lumenis Inc., 2400 Condensa St., Santa Clara, Calif. 95051, USA; Laser Indirect, manufactured by Lumenis Inc.; Opthalmascope, manufactured by Lumenis Inc.; and Acculite Probe, also manufactured by Lumenis Inc.

User interface 105, controller 107, laser control sub-system 140, laser sub-system 150, optics sub-system 165, power supply 130, cooling unit 125, and any other modules, devices, units and/or sub-systems may operate independently, interdependently, or in any combination.

Figure 2A:
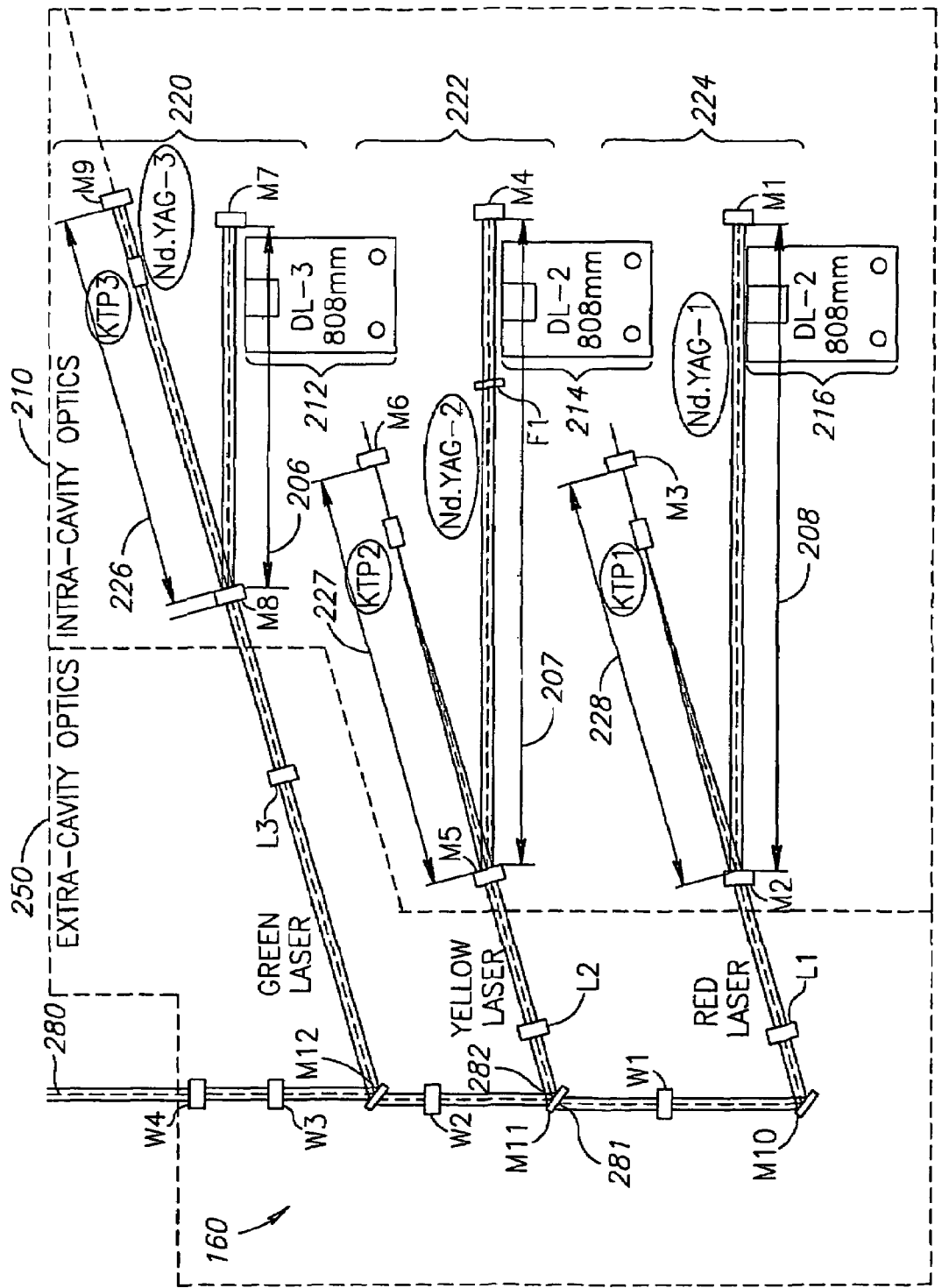
FIG. 2A is a schematic illustration of a laser sub-system of the illumination system of FIG. 1, according to some exemplary embodiments of the present invention.

FIG. 2A is a schematic illustration of a top view of laser sub-system 150, according to some embodiments of the present invention. Laser sub-system 150 may include intra-cavity optics 210, which may include one or more independent diode pumped solid-state laser cavities, for example, laser cavities 220, 222 and 224. Laser cavities 220, 222 and 224 may include independent pump diode laser sources 212, 214 and 216, respectively. These pump diode laser sources may be composed, for example, from Gallium Arsenide (GaAs), InGaAP InGaAsP, AlGaAs, or other suitable compounds. Diode lasers (e.g., DL-1. DL-2, DL-3) may serve as pump sources to emit nominal light, for example at about 808 nm, that is directed into a laser rod, for example Nd.YAG-1, Nd:YLF, Nd:YVO4, Tm:YAG, Cr:LiSAF, Er:YAG, Ti:Sapphire, Yb:SFAP or other suitable laser rods, to populate the lasing levels of the laser rods. This pumping may be accomplished, for example, by controlling the electrical power supplied to the diode pump lasers. Alternative pumping sources may be used. Each individual laser cavity may include a primary laser section, for example sections 206, 207, 208, including, for example, a laser rod (e.g., Nd:YAG-1, Nd:YAG-2, or Nd.YAG-3) to pump the initial light energy from the diodes; a frequency doubling section, for example sections 226, 227 and 228, including respective frequency doubling elements, such as, for example KTP crystals (e.g., KTP-1, KTP-2, and KTP-3), BBO, LBO, KN, LiNbO3, MgO:LiNbO3 or other suitable frequency doubling elements; mirrors (e.g., M1 to M9) and lenses (e.g., L1, L2 and L3). Laser cavities 220, 222 and 224 may respectively enable generation of laser beams at precise predetermined wavelengths, for example, about 532 nm, about 561 nm, about 659 nm, and/or any other desired laser wavelengths.

Laser cavities 220, 222 and 224, for example, may be arranged in a folded configuration. Each cavity may be defined, for example, by three mirrors: two highly reflective end mirrors (e.g., M1, M3, M4, M6, M7, and M9), and a central output fold mirror (e.g., M2, M5, and M8) that may be partially transmissive at the desired wavelength. In exemplary embodiments of the present invention cavity mirrors M1, M3, M4, M6, M7, and M9 may be designed to be highly reflective to a fundamental infrared wavelength and to the frequency-doubled wavelength. The fold mirror for each cavity, e.g., M2, M5, and M8, may additionally be coated with a suitable material to be partially transmissive to the frequency-doubled laser beam outputs, and thereby to serve as an output coupler, as is known in the art.

In the example described herein, the green laser source 212 may use, for example, an Nd:YAG rod to produce a fundamental wavelength of about 1064 nm. This wavelength may have the highest gain of the available near infrared Nd:YAG wavelengths. The green cavity mirrors (e.g., M7, M8, and M9) may therefore require no suppression of the reflectivity of other potentially competing transitions. Part of the 1064 nm light within the green laser cavity 220 may be converted to about 532 nm by the frequency doubling section 226. This 532 nm (green) light may be extracted from the green laser cavity 220 by partial transmission through the green laser output fold mirror M8. Other wavelengths in the green spectrum may be used, and other laser sources may be used.

In the example described herein, the red laser source 214 may use, for example, Nd:YAG rod to produce a fundamental wavelength of about 1319 nm. The red cavity mirrors (e.g., M1, M2, and M3) may be highly reflective at 1319 nm, but may suppress the reflectivity of other near infrared wavelengths. Part of the 1319 nm light within the red laser cavity 224 may be converted to about 659 nm by the frequency doubling section 228. The 659 nm (red) light may be extracted from the red laser cavity 224 by partial transmission through the red laser output fold mirror M2. Other wavelengths in the red spectrum may be used, and other laser sources may be used.

In the example described herein, the yellow laser source 222 may use, for example, an Nd:YAG rod to produce a fundamental wavelength of about 1123 nm. The yellow cavity mirrors (e.g., M4, M5, and M6) may be highly reflective at 1123 nm, but may suppress the reflectivity of other near infrared wavelengths. An additional optical filter F1 may be required in the yellow laser cavity 222 to suppress competing lasing lines close to 1123 nm. Part of the 1123 nm light within the laser cavity 222 may be converted to about 561 nm by, for example, frequency doubling section 224. This 561 nm (yellow) light may be extracted from the yellow laser cavity 222 by partial transmission through the yellow laser output fold mirror M5. Other wavelengths in the yellow spectrum may be used, and other types of laser sources may be used.

Laser sub-system 150 may include an extra-cavity 250 of laser sub-system 150. Extra-cavity 250 may include an optical configuration 160, which may integrate focusing and steering optics, including the various lenses, mirrors, and windows etc. described in detail below, to align the paths of independent laser beams from one or more laser cavities, such as cavities 220, 222 and 224, along a common optical axis 280, or onto a combined coaxial path. The extra-cavity portion 250 of the laser sub-system 150 may begin after the doubled frequency light passes through the fold mirror (e.g., M2, M5, M8) of laser cavities 220, 222 and 224 respectively. The beams from laser cavities 220, 222 and 224 may be collimated by lenses, for example, L1, L2, and L3, respectively, and may then be channeled along common axis 280 with the paths of the other beams using one or more combiner mirrors (e.g., M10, M11, and M12).

For example, a red laser beam may be collimated by lens L1, and then reflected by a combiner mirror M10, towards a first surface 281 of mirror M11. The combiner mirror M10, in the current example, may reflect about 659 nm light while transmitting about 1319 nm light to remove residual fundamental wavelength radiation from the 659 nm beam. The reflected beam, for example 659 nm light beam, may be referred to as the "illumination" or "treatment" beam, to be used to illuminate or treat a selected target. The angle of the combiner mirror M10 may be adjusted to align the output beam parallel to the common optical axis 280 of the extra-cavity optics 250. After reflection from combiner mirror M10, the red beam may be passed through an alignment window, e.g., window W1. Alignment window W1 may be a rotatable glass substrate having significant thickness and parallel surfaces, as is know in the art. An incident beam that is passed through the alignment window may be translated according to a selected thickness and angle, such that the output beam may be parallel to and shifted along common optical axis 280, causing a displacement of the beam that is approximately proportional to the incident angle of the beam. The angle of window W1 may be adjusted, for example, to center the path of the red beam on the path of the yellow beam, at a second surface 282 of mirror M11, at yellow combiner mirror M11.

For example, yellow laser beam may be collimated by lens L2, and then reflected by the yellow combiner mirror M11, which, in the current example, may reflect about 561 nm light while transmitting about 1123 nm light to remove residual fundamental wavelength radiation from the 561 nm beam. Combiner mirror M11 may also transmit the 659 nm red illumination beam, which may have been aligned to have a path that is in common with the yellow beam at the second surface 282 of combiner mirror M11. The angle of the yellow combiner mirror M11) may be adjusted to align the path of the yellow beam parallel to the path of the red beam. After reflection (yellow) or transmission (red) from yellow combiner mirror M11, both the yellow and red beams may pass through an alignment window W2. The angle of alignment window W2 may be adjusted to center the paths of the red and yellow beams on the path of the green beam, at an output surface of the green combiner mirror M12, in a similar way as described above with reference to mirror M11.

For example, the green laser beam may be collimated by lens L3, and then reflected by the green combiner mirror M12, which, in the current example, may reflect about 532 nm light while transmitting about 1064 nm light to remove residual fundamental wavelength radiation from the 532 nm beam. Combiner mirror M12 may also transmit the 659 nm red and 561 nm yellow illumination beams, which may have been aligned to have a path that is in common with the green beam at the output surface of combiner mirror M12. The angle of the green combiner mirror may be adjusted to align the path of the green beam substantially parallel to the path of the red and yellow beams. After reflection (green) or transmission (red and yellow) from the green combiner, all three beams may pass through an alignment window W3. The angle of alignment window W3 may be adjusted to center the paths of all three beams on the common optical axis 280 of extra-cavity optics 250.

After the paths of the laser beams with their respective wavelengths have been aligned to the common optical axis 280 of extra-cavity optics 250, the paths of the beams pass through a fourth window denoted W4 to reach the optics sub-system 165.

Figure 2B:
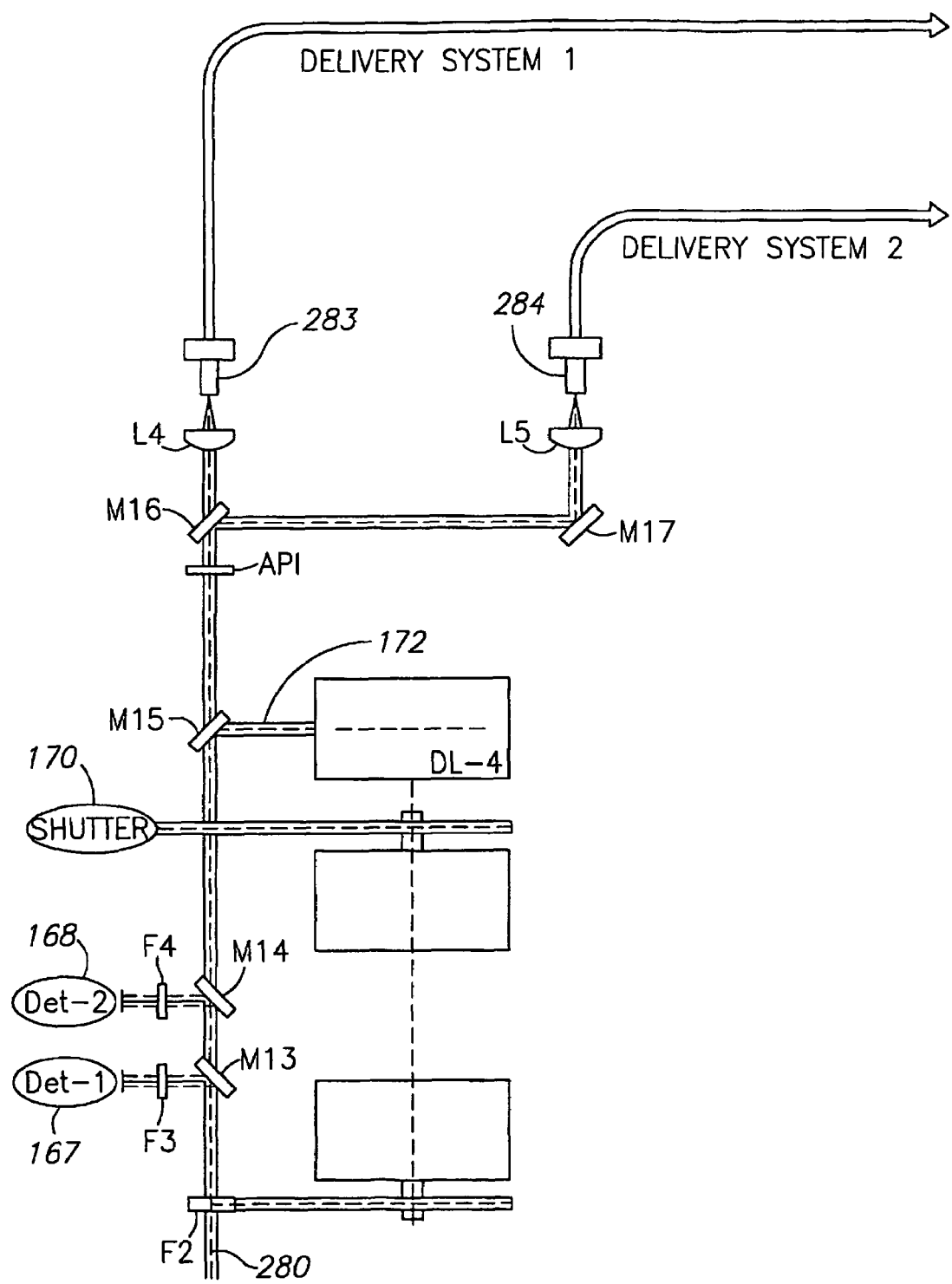
FIG. 2B is a schematic illustration of an optics sub-system of the illumination system of FIG. 1, according to some exemplary embodiments of the present invention.

FIG. 2B is a schematic illustration of optics sub-system 165 according to some embodiments of the present invention. The respective beams on the common axis 280 may be passed through an optional computer controlled moving attenuator denoted F2 to reduce the beam power when desired. The respective beams may pass through one or more power monitoring detectors (DET, DET-2), for example detectors 167 and 168, which may be, for example, a main photocell detector and a safety photocell detector, respectively, or other suitable detectors, to ensure that the required calibrated power is delivered. Each detector channel may include a mirror, for example a "pickoff" mirror (e.g., M13, or M14) that may reflect a small portion of the beams to a diffuser, such as diffuser F3 and/or F4. Diffuser F3 and/or F4 may scatter light to a photodiode, such as, for example, detectors 167 and 168. Detectors 167 and 168 may be, for example, equivalent to main photocell 167 and safety photocell 168 (of FIG. 1B).

A safety shutter 170 may be positioned after power detectors 167 and 168 to block or limit the duration of the illumination beams during, for example, system start-up and testing. Safety shutter 170 may also block the illumination beams, for example, when system 100 is in "Standby", when the emergency off switch is depressed, and/or when system errors are detected. At a mirror M15, the incoming beams may be combined with an aiming beam 172, for example, a diode-aiming beam generated by laser source DL-4. Mirror M15 may transmit the desired illumination wavelengths (e.g., 659 nm, 561 nm, and 532 nm) and reflect aiming beam 172, for example, at 635 nm. By adjustment of aiming beam combiner mirror M15, aiming beam 172 may be aligned co-axially with one or more illumination or treatment beams.

System 100 may enable directing of the laser beam output(s) to one or more selectable delivery system optical ports, such as fiber ports 283 and 284, to deliver laser energy to one or more laser delivery systems. A mechanical moving mirror M16 may be used to direct laser energy to a selected optical ports, e.g. ports 283 and 284. When delivering energy to port 283, for example, moving mirror M16 may not be placed in the beam path, and the beam energy may pass over the mirror M16, through an objective lens L4, to port 283. When delivering energy to port 284, for example, moving mirror M16 may be placed in the beam path, and may reflect incoming beams to a second mirror M17 in front of port 284. Second mirror M17 may direct the beams to the objective lens L5 of port 284. Objective lenses such as L4 and/or L5 may be used to converge the aiming and illumination beams to produce a beam waist suitable for coupling the laser energy into an optical fiber. The ports may be configured, for example, using a socket such as a format optical socket, for example a "smart nut". Such a smart nut may be a custom SubMiniature version (SMA) connector, for example, as manufactured by Amphenol, 1 Kennedy Ave, Danbury, Conn. 06810, which may provide a means for the laser system to automatically identify the type of delivery device attached to each laser port. With this delivery device identification, system 100 may activate unique features specific to this delivery device (e.g., power settings, power limits, duration settings, fluence calculators etc.). For example, a 906 SMA socket may be used, that may be aligned to center the focused laser beams on the fiber connector of the various delivery devices that may be attached to ports 283 and 284 respectively. In addition to the 906 SMA format optical socket, the optical ports may read a resistance from contacts on the delivery device SMA "smart nut". Various resistances may be used to encode the type and characteristics of the respective delivery devices attached to the respective optical ports.

Figure 3:
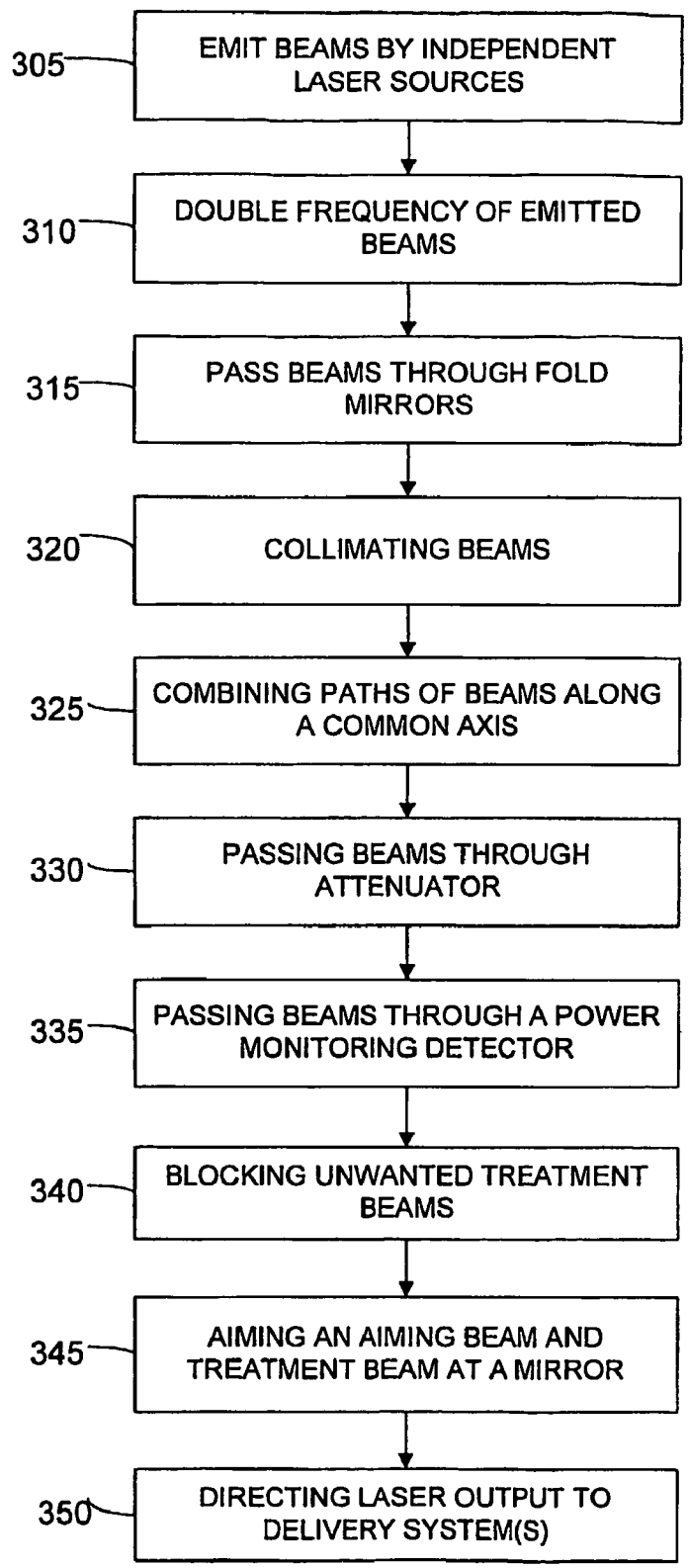
FIG. 3 is a flowchart illustration of an exemplary method for generating and delivering DPSS laser beams of two or more wavelengths by the laser illumination system of FIG. 1.

FIG. 3, in conjunction with previous FIGS. 1A, 1B, 2A and 2B, is a flowchart illustrating an exemplary method for generating and delivering beams of different wavelengths from two or more DPSS laser sources. As can be seen in FIG. 3, at block 305 nominal light beams may be generated by pumping one or more laser sources, such as pump diode lasers 212, 214 and 216, using primary laser sections, such as 206, 207 and 208, respectively. At block 310 the nominal light beams may be frequency doubled by frequency doubling sections 226, 227 and 228. At block 315 the respective frequency-doubled beams may be passed through fold mirrors M2, M5, and M8 for each laser cavity 220, 222 and 224 respectively. At block 320 the beam from each laser cavity may be collimated by a respective lens, L1, L2, and/or L3. At block 325 the paths of the respective laser beams may be combined or aligned along a common optical axis 280 by one or more combiner mirrors, e.g., M10, M11, and M12. At block 330 beams passing through the common optical axis 280 may be attenuated by passing through a moving attenuator F2. At block 335, the attenuated beams may be passed through one or more power monitoring detectors, detectors 167, 168, to detect whether an output beam's power is at an acceptable level, relative to a predetermined power level. Such detection may be achieved by reflecting at least a portion of an output beam to a diffuser, e.g., F3, F4, by one or more pick-off mirrors M13, or M14, and by scattering a reflected portion of the beam from diffuser F3, F4, to pass the scattered light through at least one photodiode, e.g., detectors 167, 168. At block 340 beams, for example unwanted illumination beams, may be blocked out or limited by a safety shutter 170. At block 345 an aiming beam 172 generated by laser source DL-4 may be aimed at a mirror M15, together with the illumination beam from laser cavities 220, 222 or 224, to align the aiming beam 172 with the selected illumination beams. At block 350 the laser beams may be directed to one or more delivery systems for delivery of laser energy to one or more selected targets.

Any combination of the above steps may be implemented. Further, other steps or series of steps may be used.

Figure 4:
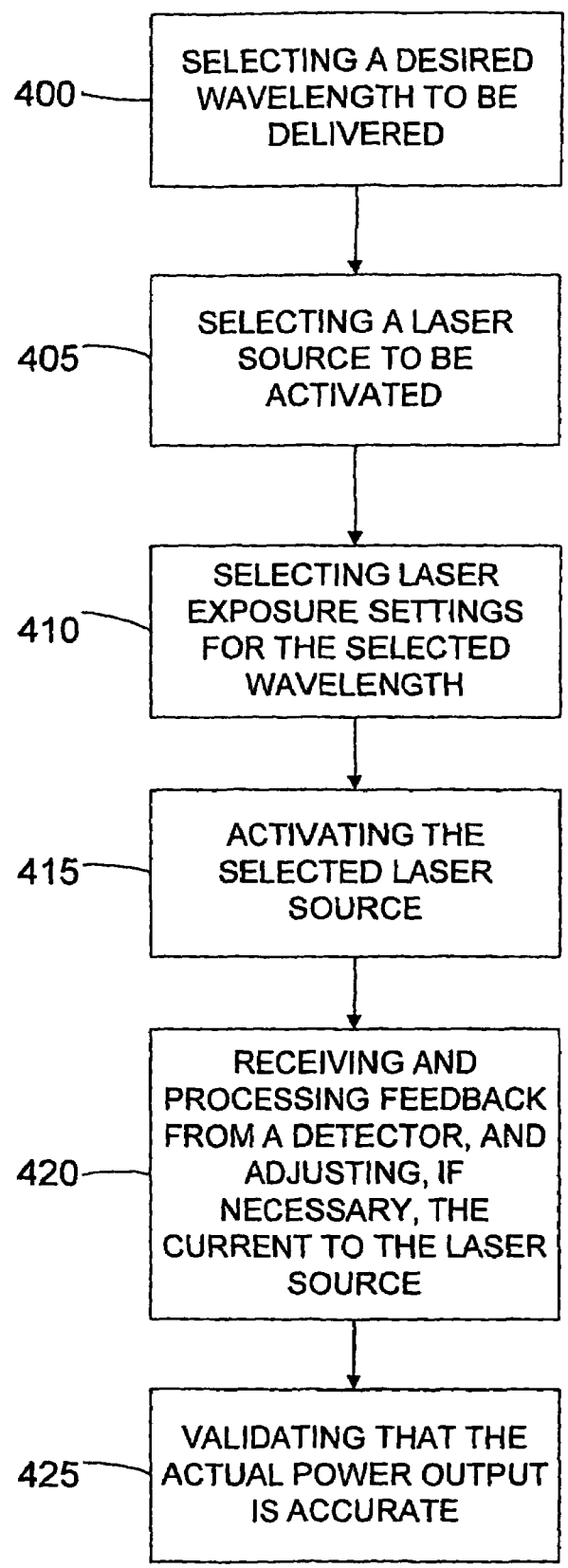
FIG. 4 is a flowchart illustrating an exemplary method for operating a laser illumination system at one or more selected wavelengths in accordance with embodiments of the present invention.

Reference is now made to FIG. 4, which is a flow chart illustrating an aspect of an exemplary method for controlling laser output by the laser illumination system of FIG. 1. The method may include: At block 400, performing selection of a desired wavelength to be delivered. At block 405 selecting a laser source to be activated, corresponding to the selected wavelength. At block 410 selecting laser exposure settings for the selected wavelength (block 400), which may include parameters such as power, exposure duration, and treatment intervals etc. At block 415 activating the selected laser source to generate a laser beam with the required wavelength. At block 420 receiving appropriate feedback from a detector, such as main detector 167, and processing the data received. For example, the actual power output may be compared to the desired power parameters. The laser output by the selected laser source may be adjusted, if necessary, according to one or more laser output power parameters, for example, by altering the pump diode current to match the required power level. At block 425, validating that the actual power output is accurate, for example, by comparing safety detector results to the results from the a detector such as main detector 167. Block 425 may be executed simultaneously with block 420.

Any combination of the above operations may be implemented, and any number of the above operations may be implemented. Further, other operations or series of operations may be used.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A medical laser system for applying laser energy to a target ophthalmic tissue of a human for medical purposes, the improvement comprising:
    a first source of green laser light;
    a first light path associated with the first source;
    a second source of yellow laser light;
    a second light path associated with the second source;
    a third source of red laser light;
    a third light path associated with the third source;
    a controller to control the activation of any of the first, the second and the third laser light sources;
    an optical configuration to selectively align any of the first, the second and the third light paths along a common axis;
    an output port to receive the aligned light beam from the common axis; and
    wherein the light from the output port is directed to a target ophthalmic tissue;
    a selector operatively associated with the controller for selecting one of said first, second and third laser light sources;
    a selector operatively associated with the controller for setting laser exposure settings for the selected laser light source; and
    an activator operatively associated with the controller to cause the selected laser source to generate a light beam.

2. The laser system of claim 1 wherein the first source of green laser light has a wavelength of about 532 nm.

3. The laser system of claim 1 wherein the second source of yellow laser light has a wavelength of about 561 nm.

4. The laser system of claim 1 wherein the third source of red laser light has a wavelength of about 659 nm.

5. The laser system of claim 1 wherein that tissue is targeted for photocoagulation purposes.

6. The laser system of claim 1 wherein the output port is directed to an opthalmoscope.

7. The laser system of claim 1 wherein the output port is directed to a slit-lamp assembly.

8. The laser system of claim 1 wherein the output port is directed to an endophotocoagulation probe.

9. The system of claim 1, wherein at least one of said sources of laser light comprises a primary laser section and a frequency doubling section.

10. The system of claim 1, wherein at least one of said sources of laser light comprises a pump diode laser source.

11. The system of claim 1, wherein said optical configuration comprises at least one fold mirror.

12. The system of claim 1, wherein said optical configuration comprises one or more combiner mirrors to combine the light paths.

13. The system of claim 1, comprising a plurality of optical ports associated with the output of said optical configuration.

14. The apparatus of claim 1, comprising a moving attenuator to attenuate at least one of said sources of laser light.

15. The apparatus of claim 1, comprising at least one power-monitoring detector to detect the power of at least one of said sources of laser lights on said common axis.

16. The apparatus of claim 1, comprising at least one pick-off mirror to reflect at least one or more of said sources of laser light to a diffuser.

17. The apparatus of claim 1, comprising a safety shutter to limit the exposure of said target ophthalmic tissue to one or more of said sources of laser light.

18. The apparatus of claim 1, comprising an aiming beam to enable aiming of said aligned light beam towards the target ophthalmic tissue.

19. The apparatus of claim 1, further comprising:
    a detector positioned in one or more of said light paths;
    a feedback circuit for processing detected light from the laser light source; and
    a circuit for validating the accuracy of the actual power output of the generated light beam.

20. The laser system of claim 1 further comprising at least one collimation lens to collimate one or more of the first, second or third light sources.

21. The laser system of claim 1 wherein the selector selects two of the first, second and third laser light sources.

22. A method of treating ophthalmic tissue of a human being with a laser system, comprising the steps of:
    providing first, second and third sources of green laser light, yellow laser light and red laser light, respectively;
    providing first, second and third light paths associated with each of the laser light sources;
    providing a controller to control the activation of any of the first, second and third laser light sources to the ophthalmic tissue depending on the type of treatment;
    providing an optical configuration to allow selective alignment of the light paths of any of the first, the second and the third laser light along a common axis; and
    providing an output port to receive the selected activated laser light beam from the common axis and direct the beam to the ophthalmic tissue of a human being;
    selecting one of said first, second and third laser light sources with a selector operatively associated with the controller;
    selecting laser exposure settings for the selected laser light source with a selector operatively associated with the controller; and activating the selected laser source to generate a light beam with a selector operatively associated with the controller.

23. The method of claim 22, further comprising delivering an aiming beam substantially along said aligned light path.

24. The method of claim 22, comprising channeling said two or more laser light paths via one or more optical ports.

25. The method of claim 22, comprising delivering said laser light paths using one or more delivery systems.

26. The method of claim 22, further comprising:
providing a detector in one or more of said light paths;
processing feedback from the detector, for said generated light beam; and
validating accuracy of the actual power output of said generated light beam.

27. The method of claim 22, wherein the first source of green laser light has a wavelength of about 532 nm.

28. The method of claim 22, herein the second source of yellow laser light has a wavelength of about 561 nm.

29. The method of claim 22, wherein the third source of red laser light has a wavelength of about 659 nm.

* * * * *